United States Patent [19]

McCaffrey et al.

[11] Patent Number: 4,612,405
[45] Date of Patent: Sep. 16, 1986

[54] CONTINUOUS SORPTION PROCESS

[75] Inventors: David J. A. McCaffrey, Cheltenham; Percy E. Rogers, Derby; James Carlton, Cheltenham, all of England

[73] Assignee: Coal Industry (Patents) Ltd., London, England

[21] Appl. No.: 737,206

[22] Filed: May 23, 1985

[51] Int. Cl.[4] .................. C07C 29/76; C07C 31/08
[52] U.S. Cl. .................................... 568/916; 568/917
[58] Field of Search ............................... 568/916, 917

[56] References Cited

U.S. PATENT DOCUMENTS

| | | | |
|---|---|---|---|
| 2,472,912 | 6/1949 | McCarter | 568/916 |
| 4,343,623 | 8/1982 | Kulprathipanja et al. | 568/917 |
| 4,351,732 | 9/1982 | Psaras et al. | 568/916 |
| 4,373,935 | 2/1983 | Ausikaitis et al. | 568/917 |

FOREIGN PATENT DOCUMENTS 2096125 10/1982 United Kingdom .

Primary Examiner—J. E. Evans
Attorney, Agent, or Firm—Stevens, Davis, Miller & Mosher

[57] ABSTRACT

A process providing continuous or quasi-continuous sorption uses at least three fixed bed sorbent zones connectable in series by pipes, for the passage of a liquid phase containing a component to be sorbed. The approach of saturation of one or more of the zones is detected, e.g., using temperature sensors, and regeneration of the saturated zone or zones is initiated using hot gas. Compared to conventional sorption processes, energy savings, especially as regards energy consumed in blowing the hot gas through the fixed bed zone, are obtainable.

6 Claims, 1 Drawing Figure

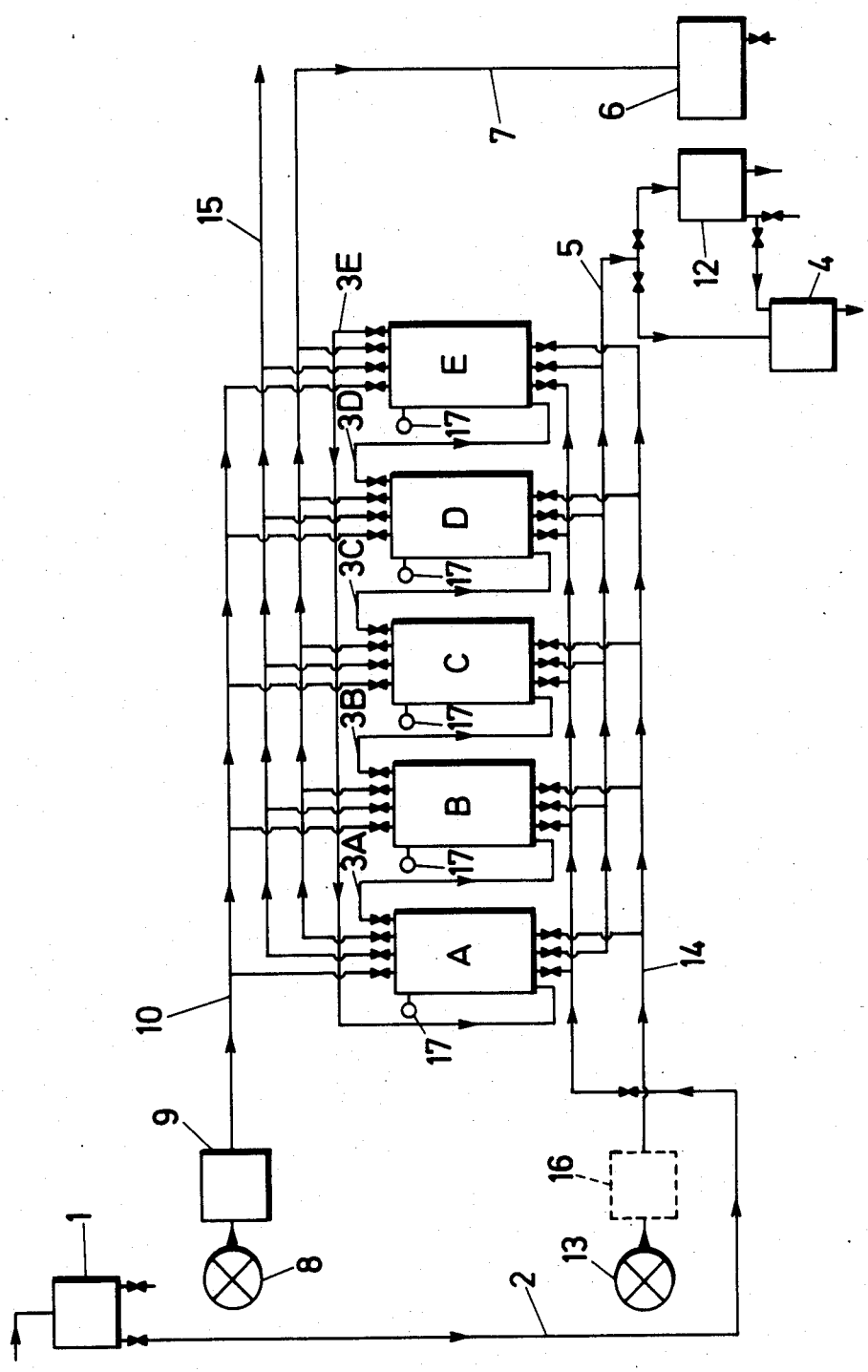

CONTINUOUS SORPTION PROCESS

This invention concerns a continuous sorption process.

Sorption processes are essentially batch-type processes, in which a charge of sorbent has passed therethrough a fluid, one or more components of which are sorbed. Eventually, if the process is run for sufficiently long, the sorbent becomes saturated and break through of the component occurs. At or before this time, the charge of sorbent has to be regenerated in some way by treatment to release the sorbed component. In the case of the purification of organic fluids containing water or another fluid using a fixed bed sorbent such as a natural or synthetic zeolite which occludes the water or another fluid of smaller molecular cross-section than the organic fluid, the regeneration step can in fact take a considerable time, well in excess of that required for the sorption. For example, in the purification of ethanol/water mixtures, regeneration or desorption is carried out generally by a hot gas, and taking into account the time required to raise the temperature of the sorbent bed and the cooling time necessary so that the sorbent bed can effectively handle liquid ethanol/water mixtures in a further cycle of operation, the regeneration time may form 70% of the total operation of a single column. It is, of course, well known to operate various processes utilising a column which requires regeneration of its contents by having a further column in parallel, and switching from one to another. However, it is not economic in sorption processes to have one column being used for sorption while three are in various stages of regeneration, as would be required for continuous operation.

British Patent Specifications Nos. 879,687 and 889,100 address themselves to continuous soption process, in which a fixed bed sorbent process is operated by dividing the bed into four serially connected zones. It is clear that each zone is essentially the same size, and that hence in the particular system mentioned above, regeneration could not be completed in the time available. In addition, this prior process requires a continuous cyclic circulation of a fluid which must include some of the desorption fluid. A complex valve arrangement is suggested, which is driven at fixed time intervals.

The present invention provides a quasi-continuous or continuous sorption process requiring a hot gas regeneration step, comprising the use of a least three fixed bed sorbent zones connectable in series for the passage of a liquid phase containing a component to be sorbed, detecting the approach of saturation of one or more of the said zones and initiating regeneration using hot gas of said one or more of said zones upon said detection, optionally while passing the liquid phase through one or more other fixed bed sorbent zones, provided that if more than one zone is regenerated, the hot gas flows are in parallel and not in series.

The invention offers, in its simplest form, the possibility of energy saving and the reduction of regeneration time to about 50% of the cycle time. It is conventional to design a sorption system to have a column with sufficient capacity to give an adequate treatment time before regeneration is required. We have now found that if at least three sorbent zones are employed, each of which is appreciably smaller than a conventional single column, regeneration using hot gas is facilitated. In one embodiment, the process may be thought of as using four "quarter columns", that is each zone is a quarter of the length of the nominal standard column for the duty required. The plant is arranged so that with serial connection, the first three zones become saturated and before complete saturation of the final zone, the feed is stopped and all zones are regenerated in parallel. Accordingly, the pressure drop of hot gas across the total sorbent bed is a quarter of that of the total bed considered in series; the power consumption of the blowers required for the gas is therefore considerably reduced and significant energy savings result. Furthermore, the regeneration time is reduced to about 50% of the cycle time, and either the process can operate on a quasi-continuous basis using a single train of four or more columns, possibly using a feed storage tank for the liquid phase, or using two trains in parallel, one being regenerated and the other carrying out sorption. This latter enbodiment still results in decreased cycle times and permits continuous operation with reduced capital costs and energy costs compared to conventional columns.

It will be appreciated that the three or more zones may each occupy a fixed bed column or may form discrete zones in a single column; all that is required is that the necessary pipework is provided and each zone is adequately separated. Although the separation of a single column into zones according to the invention may involve less capital costs than three or more individual columns, in some circumstances, for example, for reasons of space, it may be advantageous to use a number of columns.

In a further embodiment of the invention, a group of five zones is provided, three of which operate in series in the sorption mode while the remaining two zones are regenerated using hot gas and cooled. Completely continuous operation is possible, apart from switching time. Experience with a particular feedstock will be sufficient to determine suitable feed rates and regeneration conditions which enable substantially complete regeneration of the fifth zone in the time available, which is the time taken for first of the series of zones to reach substantial saturation. When the first of the series of zones is saturated, it is regenerated and the second of the series is fed with the feedstock, the freshly regenerated and cooled zone being connected in series as the third member of the series. Each zone thus undergoes a complete cycle of operation. Each zone may, as mentioned above, be a discrete zone in a single column or occupy an individual column.

The detection of saturation of a zone in the present invention may be done in a number of ways, including analysis, for example by gas-liquid chromatography, for the level of the component to be sorbed. Preferably, however, the temperature at the exit level of the bed in each zone is monitored, and the approach of saturation is determined by a rise in temperature.

It is preferred in most cases to include in the regeneration step for each zone a cooling step, suitably by blowing a cool gas therethrough. Energy savings are also possible according to the invention in this cooling step.

The invention will now be illustrated with reference to the accompanying drawing, in which a plant incorporating one embodiment of the invention is schematically shown. Valves are shown in conventional manner.

The plant has five equal-sized columns A, B, C, D and E, each containing an equal amount of a zeolite adsorbent capable of adsorbing water from an ethanol/water mixed feedstock. The feedstock is supplied from a constant head tank 1, by line 2, to any of the columns. Each column has a line 3, enabling it to be connected in series to the next, and column E can be connected by line 3E to column A. Each column is also connected to a drain tank 4, by a line 5, and to a product tank 6, by a line 7.

The regeneration equipment includes a blower 8, and a heat exchanger 9, which is effective to raise the temperature of air to 260°–300° C., and connected to the top of each column by line 10. The line 5, from the bottom of each column carries the exiting regeneration gases; these gases are directed to a condensor, 12. A second blower 13, or optionally the blower 8, is connected by line 14, to each column to provide cooling air to cool the regenerated column down to below 80° C. before it is ready for the next part of the cycle of operation. The cooling air is taken by line 15 to a stack (not shown) and the regeneration gases from the condensor 12 also pass to the stack. A cooler 16, indicated in broken lines, may cool the cooling air further, if required.

Each column has at least one temperature indicator 17, connected to display and control devices capable of detecting the approach of saturation and initiating a switch to regeneration.

In operation, one column, say column D, has been saturated and is now being regenerated. The ethanol/water feedstock from constant head tank 1 is fed to the bottom of column A through line 2, the other valves on line 2 being closed. Liquor leaving column A passes through line 3A to column B, and so on, until the liquor from column C, being essentially pure ethanol, is taken by line 7 to the product tank 6.

Column D, having first of all its liquid feed lines shut off, is allowed to drain into drain tank 4; the liquor drained, because of the saturation of the sorbent, is essentially unpurified, and is returned to the feedstock head tank 1. Thereafter, hot air is blown through line 10 into column D and leaves through line 5. Initially, the hot air removes the ethanol-rich phase still clinging to particles of absorbent. The second portion of the hot air, heats up the bed of adsorbent to about 260° C. and the water vapour in the micropores of the adsorbent is driven off and condensed in condensor 12. After essentially no more water vapour is driven off, the hot air blast is shut off and cool air from line 14 is employed to cool the column D down to below 80° C. so that it is ready to adsorb water again from the feedstock. This complete regeneration takes rather less than the time for both column A and, in turn, column B to become exhausted. Column E is always maintained one stage ahead of column D, and undergoes the later portion of its regeneration at the same time as the earlier portion of the regeneration of column D.

It is important that the stepwise progression of each column throughout the cycle of operation is maintained, and this may conveniently be done by an electro-mechanical interlock and control mechanism for the many valves employed.

We claim:

1. A quasi-continuous or continuous sorption process requiring a hot gas regeneration step, comprising passing a liquid phase containing a component to be sorbed through at least three fixed bed sorption zones connected in series, detecting the approach of saturation of all of said zones, stopping the flow of liquid through the zones upon detection of the approach of saturation of the final zone, and initiating regeneration using hot gas through said zones upon said detection, all said zones being regenerated in parallel.

2. The process according to claim 1, wherein a train of four or five absorption zones are used.

3. The process according to claim 1, wherein said liquid phase comprises water and an organic solvent.

4. The process according to claim 3, wherein said organic solvent is an alcohol.

5. The process according to claim 1, wherein the approach of saturation of a sorption zone is detected by monitoring the temperature of the zone.

6. A quasi-continuous or continuous sorption process using five fixed bed sorption zones requiring a hot gas regeneration step, comprising continuously passing a liquid phase containing a component to be sorbed through three of said five fixed bed sorption zones connected in series while initiating regeneration of the remaining two saturated zones by passing hot gas through said remaining two zones, said hot gas flowing through said zones in parallel and detecting the approach of saturation of at least one of said zones through which the liquid phase is passing for regeneration.

* * * * *